United States Patent
Gill et al.

(10) Patent No.: US 11,219,767 B2
(45) Date of Patent: Jan. 11, 2022

(54) METHOD FOR DETECTING POCKET STABILITY FOR AN IMPLANTABLE CARDIAC MONITOR

(71) Applicant: PACESETTER, INC., Sytlmar Sylmar, CA (US)

(72) Inventors: Jong Gill, Valencia, CA (US); Fujian Qu, San Jose, CA (US); Stuart Rosenberg, Woodbury, MN (US)

(73) Assignee: Pacesetter, Inc., Sylmar, CA (US)

( * ) Notice: Subject to any disclaimer, the term of this patent is extended or adjusted under 35 U.S.C. 154(b) by 192 days.

(21) Appl. No.: 16/224,546

(22) Filed: Dec. 18, 2018

(65) Prior Publication Data
US 2020/0188664 A1    Jun. 18, 2020

(51) Int. Cl.
| | | |
|---|---|---|
| *A61N 1/36* | (2006.01) | |
| *A61N 1/362* | (2006.01) | |
| *A61B 5/363* | (2021.01) | |
| *A61N 1/372* | (2006.01) | |
| *A61B 5/053* | (2021.01) | |
| *A61N 1/37* | (2006.01) | |
| *A61N 1/39* | (2006.01) | |
| *A61B 5/287* | (2021.01) | |

(52) U.S. Cl.
CPC ............ *A61N 1/3627* (2013.01); *A61B 5/363* (2021.01); *A61N 1/3621* (2013.01); *A61B 5/053* (2013.01); *A61B 5/287* (2021.01); *A61N 1/3706* (2013.01); *A61N 1/37252* (2013.01); *A61N 1/39622* (2017.08)

(58) Field of Classification Search
CPC ........ A61B 5/0215; A61B 5/686; A61N 1/36; A61N 1/3627
See application file for complete search history.

(56) References Cited

U.S. PATENT DOCUMENTS

| | | | |
|---|---|---|---|
| 8,868,165 B1 * | 10/2014 | Nabutovsky | A61B 5/0538 600/515 |
| 2011/0213261 A1 | 9/2011 | Naware et al. | |
| 2013/0211205 A1 | 8/2013 | Havel et al. | |
| 2015/0005862 A1 * | 1/2015 | Kroll | A61N 1/0563 607/122 |

* cited by examiner

*Primary Examiner* — Michael J D'Abreu
(74) *Attorney, Agent, or Firm* — The Small Patent Law Group LLC; Dean D. Small

(57) ABSTRACT

A computer implemented method for detecting pocket stability for an implantable cardiac monitor, including under control of one or more processors in the ICM, collecting impedance data over at least one cardiac cycle. The impedance data is processed to separate an impedance waveform that varies over the at least one cardiac cycle in a manner representative of cardiac functionality over the at least one cardiac cycle. A characteristic of interest is analyzed from the impedance waveform over the at least one cardiac cycle. A pocket stability state of the ICM is identified and recorded based on the analyzing operation.

19 Claims, 6 Drawing Sheets

METHOD FOR DETECTING POCKET STABILITY FOR AN IMPLANTABLE CARDIAC MONITOR

BACKGROUND

Embodiments of the present disclosure generally relate to systems and methods for detecting pocket stability of an implantable cardiac monitor (ICM), and more particularly to utilizing an impedance waveform to determine changes in the pocket stability.

An implantable medical device (IMD) is a medical device that is configured to be implanted within a patient anatomy and commonly employs one or more leads with electrodes that either receive or deliver voltage, current or other electromagnetic pulses from or to an organ or tissue for diagnostic or therapeutic purposes. Such IMDs include ICMs used to monitor the heart and are positioned within a pocket of tissue within the patient.

However, the ICM positioning in the pocket, and the pocket itself can change characteristics, effecting measurements. In particular, despite being tightly secured within the pocket, the ICM can still move and reposition within the pocket, effecting the ICM reading. Additionally, fluid levels and tissue variances within the pocket similarly can cause reading variation for the ICM. When these reading fluctuations occur, the ICM can obtain an incorrect reading and trigger an inappropriate arrhythmia or brady episode suggesting that a patient's heart has temporarily stopped when instead a pocket change has occurred.

BRIEF SUMMARY

In accordance with embodiments herein, a computer implemented method for detecting pocket stability for an implantable cardiac monitor (ICM). The method includes, under control of one or more processors in the ICM, collecting impedance data over at least one cardiac cycle, and processing the impedance data to separate an impedance waveform that varies over the at least one cardiac cycle in a manner representative of cardiac functionality over the at least one cardiac cycle. The method also includes analyzing a characteristic of interest from the impedance waveform over the at least one cardiac cycle, and identifying and recording a pocket stability state of the ICM based on the analyzing operation.

Optionally, the method includes processing the impedance data to separate a subsequent impedance waveform, and comparing the subsequent impedance waveform to a base-line impedance waveform. Optionally, comparing the subsequent impedance waveform to the base-line impedance waveform comprises comparing the characteristic of interest from the processed impedance waveform and a characteristic of interest from the subsequent impedance waveform to determine a change in the pocket stability state of the ICM. Also, optionally, the characteristic of interest of the processed impedance waveform is at least one of a morphology characteristic or a timing characteristic.

Optionally, the method also includes, recording electrocardiogram (EGM) signals at electrodes provided on a housing of the ICM and detecting a pause or stoppage based on the recorded EGM signals. In an example, the method also includes, processing the impedance data to separate a subsequent impedance waveform, and comparing the subsequent impedance waveform to the base-line impedance waveform that is based on the processed impedance waveform, is responsive to the ICM detecting the pause or stoppage. Additionally and optionally, the method includes determining whether the pause or stoppage is false by comparing the subsequent impedance waveform to the base-line impedance waveform, outputting an indicator that the ICM has shifted within an implant pocket and is experiencing degradation of signal quality of the EGM signals when the pause or stoppage is false, and discarding the detected pause or stoppage when the pause or stoppage is false. In one example the indicator is an alert signal that provides a communication from the ICM related to the change in pocket stability state. Optionally, the communication is displayed on a display of the ICM with a label formed based on comparing the base-line impedance waveform and subsequent impedance waveform. In another example the impedance waveform is based on an alternating current (AC) based signal.

In accordance with embodiments herein, a monitoring system for detecting pocket stability for an implantable cardiac monitor (ICM), including an ICM with a housing and one or more processors for receiving impedance data generated by an alternating current (AC) signal of the ICM. The one or more processors are configured to separate from the data generated by the AC signal an impedance waveform that varies over the at least one cardiac cycle in a manner representative of cardiac functionality over the at least one cardiac cycle, analyze a characteristic of interest from the impedance waveform over the at least one cardiac cycle, and identify and record a pocket stability state of the ICM based on the characteristic of interest.

Optionally, the one or more processors are further configured to record electrocardiogram (EGM) signals at electrodes provided on the housing of the ICM, detect a pause or stoppage based on the recorded EGM signals, determine whether the pause or stoppage is false by comparing the subsequent impedance waveform to the base-line impedance waveform; and outputting an indicator that the ICM has shifted within the implant pocket and is experiencing degradation of signal quality of the EGM signals when the pause or stoppage is false. The one or more processors are optionally further configured to, prior to outputting the indicator, process the impedance data to separate a subsequent impedance waveform, and compare the subsequent impedance waveform to the base-line impedance waveform.

Optionally, the one or more processors are also further configured to, determine a change in pocket stability state based on the comparison of the subsequent impedance waveform to the base-line impedance waveform; and responsive to the change in pocket stability state of the ICM, transmitting an alert signal to provide a communication from the ICM related to the change in pocket stability state. Additionally, the change in pocket stability state of the ICM is above a threshold value.

In accordance with embodiments herein, a computer implemented method for detecting pocket stability for an implantable cardiac monitor (ICM), the method including under control of one or more processors, forming a base-line impedance waveform and base-line pocket stability state based on historical data, and collecting impedance data from an alternating current (AC) signal over at least one cardiac cycle. The method also includes processing the impedance data to separate an impedance waveform from at least one cardiac cycle in a manner representative of cardiac functionality over the at least one cardiac cycle, and analyzing a characteristic of interest from the impedance waveform over the at least one cardiac cycle to determine a pocket stability state. After determining the pocket stability state, comparing the pocket stability state based on the historical data and the pocket stability state determined from the processed impedance waveform to determine a change in pocket stability state.

Optionally, the method includes recording electrocardiogram (EGM) signals at electrodes provided on a housing of the ICM, detecting a pause or stoppage based on the recorded EGM signals, determining whether the pause or stoppage is false by comparing a subsequent impedance waveform to the base-line impedance waveform, and outputting an indicator signal that the ICM has shifted within an implant pocket and is experiencing degradation of signal quality of the EGM signals when the pause or stoppage is false.

In another example the method also includes wherein analyzing the characteristic of interest from the impedance waveform over the at least one cardiac cycle to determine a pocket stability state comprises comparing the characteristic of interest from the processed impedance waveform and a characteristic of interest from the historical data.

Optionally, the method further includes wherein the characteristic of interest of the processed impedance waveform amplitude is at least one of impedance waveform, impedance waveform slope, impedance waveform amplitude, or impedance waveform peak-to-peak value. In another example, the historical data includes impedance waveform morphology data.

DETAILED DESCRIPTION

Figure 1:
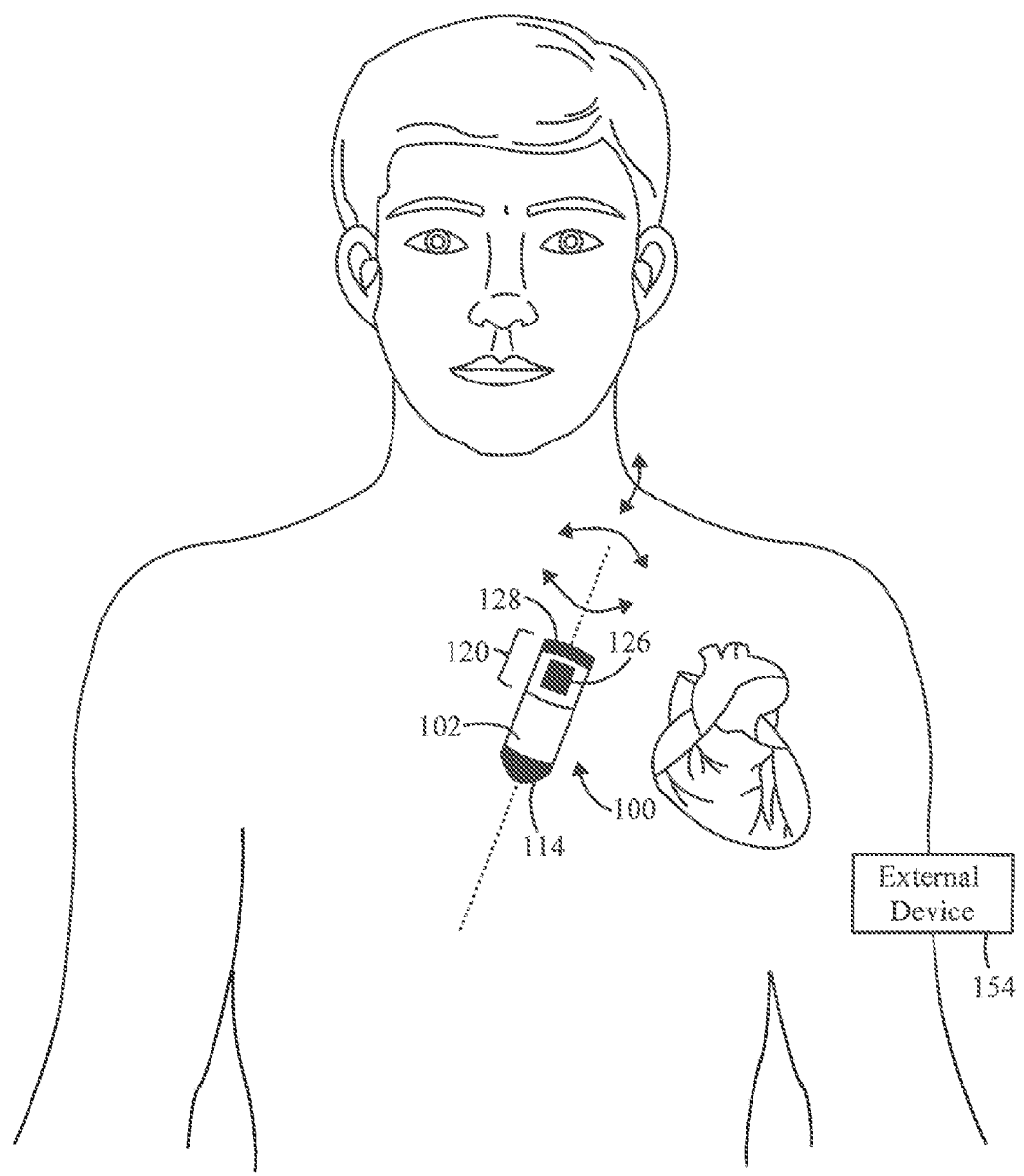
FIG. 1 illustrates an implantable cardiac monitoring device (ICM) intended for subcutaneous implantation at a site near the heart in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method and System to Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device" and U.S. Pat. No. 9,232,485 "System And Method For Selectively Communicating With An Implantable Medical Device", which are hereby incorporated by reference.

Additionally or alternatively, the IMD may include one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties.

Further, one or more combinations of IMDs may be utilized from the above incorporated patents and applications in accordance with embodiments herein.

The methods and systems described herein may employ all or portions of structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, where indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

When computer implemented methods are described herein, including through implementation with one or more processors, instructions for such one or more processors, may be received from the cloud storage environment. Additionally and alternatively, the computer implemented methods, including through implementation through one or more processors in one example includes implementation within the cloud environment and transmission of data packets from the cloud to an IMD or external device.

FIG. 1 illustrates an example implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias, pauses, Brady episodes and the like and if a pause, Brady episode, arrhythmia, and the like is detected, automatically records the CA signals in memory for subsequent transmission to an external device or external instrument (EI) 154. The CA signal processing and detection is provided for, at least in part, by algorithms embodied in or implemented by one or more microprocessors in the ICM 100. The ICM 100 includes one or more processors and memory that stores program instructions directing the processors to implement arrhythmia, including atrial fibrillation (AF), pause, Brady episode, and the like detection utilizing an onboard R-R interval irregularity (ORI) process that analyzes cardiac activity signals collected over one or more sensing channels.

As explained herein, the ICM 100 includes electrodes that collect cardiac activity (CA) signals in connection with multiple cardiac beats and in connection with different IMD locations (e.g., different positions and/or different orientations). The ICM may change location within a subcutaneous pocket relative to an initial implant position through translation and/or rotation, such as i) moving up and down (elevating/heaving) within the subcutaneous pocket; ii) moving left and right (strafing/swaying); iii) moving forward and backward (walking/surging); iv) swiveling left and right (yawing); v) tilting forward and backward (pitching); vi) rotation clockwise and counterclockwise; and vii) pivoting side to side (rolling).

The ICM 100 includes one or more sensors to collect acceleration signatures that are indicative of heart sounds produced at different points in a cardiac cycle. One or more processors of the ICM group the acceleration signatures associated with first and second sets of cardiac beats into a corresponding posture bin based on the device location information. The processors of the ICM identify at least one of differences and/or similarities between the acceleration signatures in a first posture bin (and/or other posture bins) in connection with treating a heart condition. The sensor can also detect posture and activity of patients.

Figure 2:
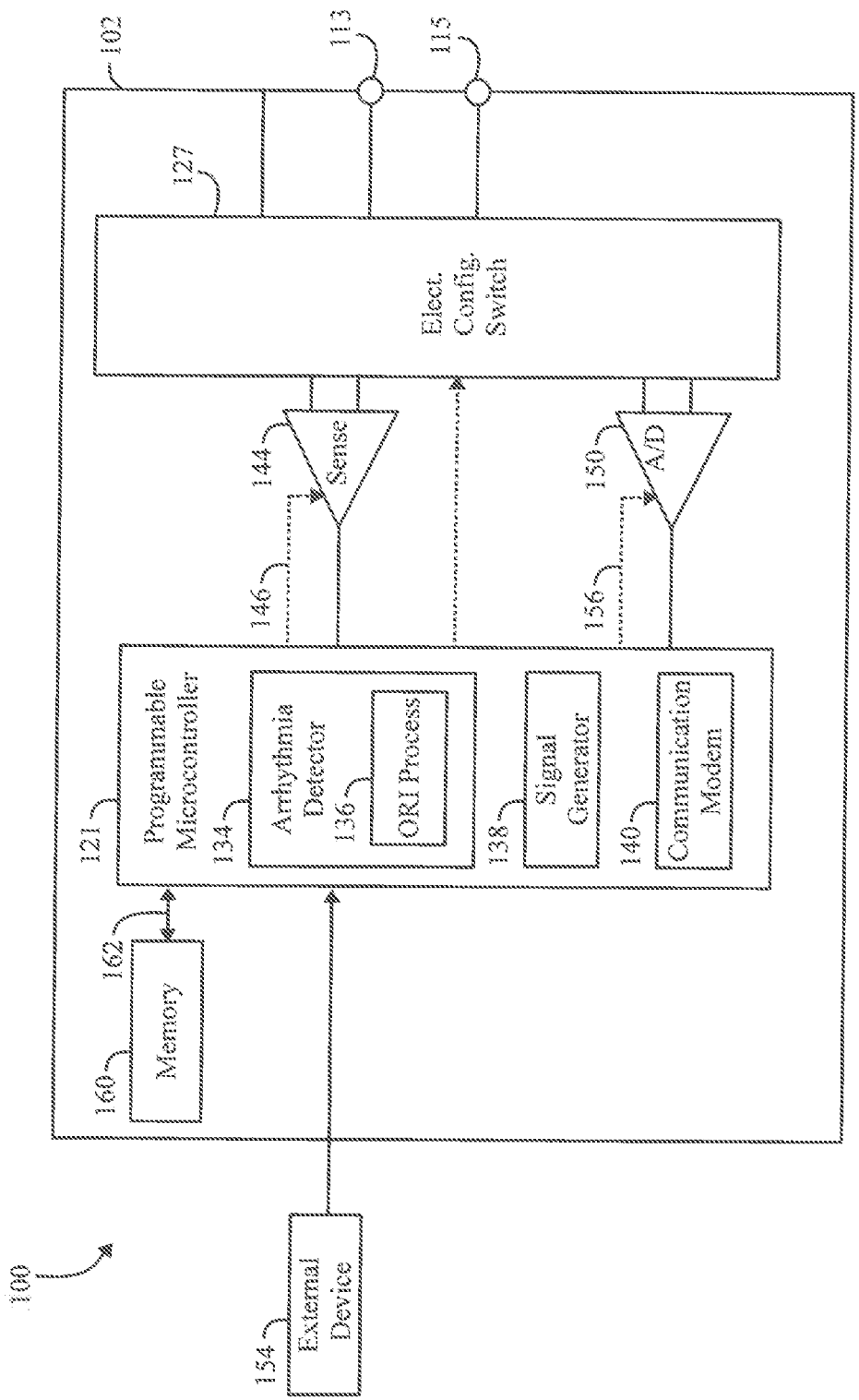
FIG. 2 illustrates a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can," "case," "encasing," or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is also equipped with a signal generator 138. The signal generator in one example includes circuitry operated and controlled by the programmable microcontroller 121 to provide a signal across housing electrodes including electrodes 114 and 126 such that an impedance waveform may be measured therefrom. In one example the signal generator 138 provides an AC current signal across the electrodes 114 and 126. In other examples the AC current signal may be varied by the signal generator 138. The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

In the example of FIG. 1, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or a bipolar sensing configuration. Optionally, the sensing circuit 144 may be removed entirely, and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. For example, the ORI process 136 may implement the AF detection methods described in U.S. Pat. No. 8,135,456, titled "Device and Method for Detecting Atrial Fibrillation" the complete subject matter of which is incorporated herein by reference in its entirety.

The ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, activity sensing or other physiological sensors, and electrode polarity, etc.

The ICM 100 may also collect and utilize impedance data to monitor and determine the positioning of the ICM 100 within its pocket. The impedance measured may be expressed in terms of ohms. Alternatively, the impedance may be expressed as an admittance measurement. The admittance may be inversely related to the impedance. The impedance measured may vary based on a variety of factors, including the amount of fluid in the pocket and shifts of the ICM in the pocket. Therefore, change in impedance waveforms (IWs) may be utilized to determine movement of the ICM 100 within the pocket.

Figure 3:
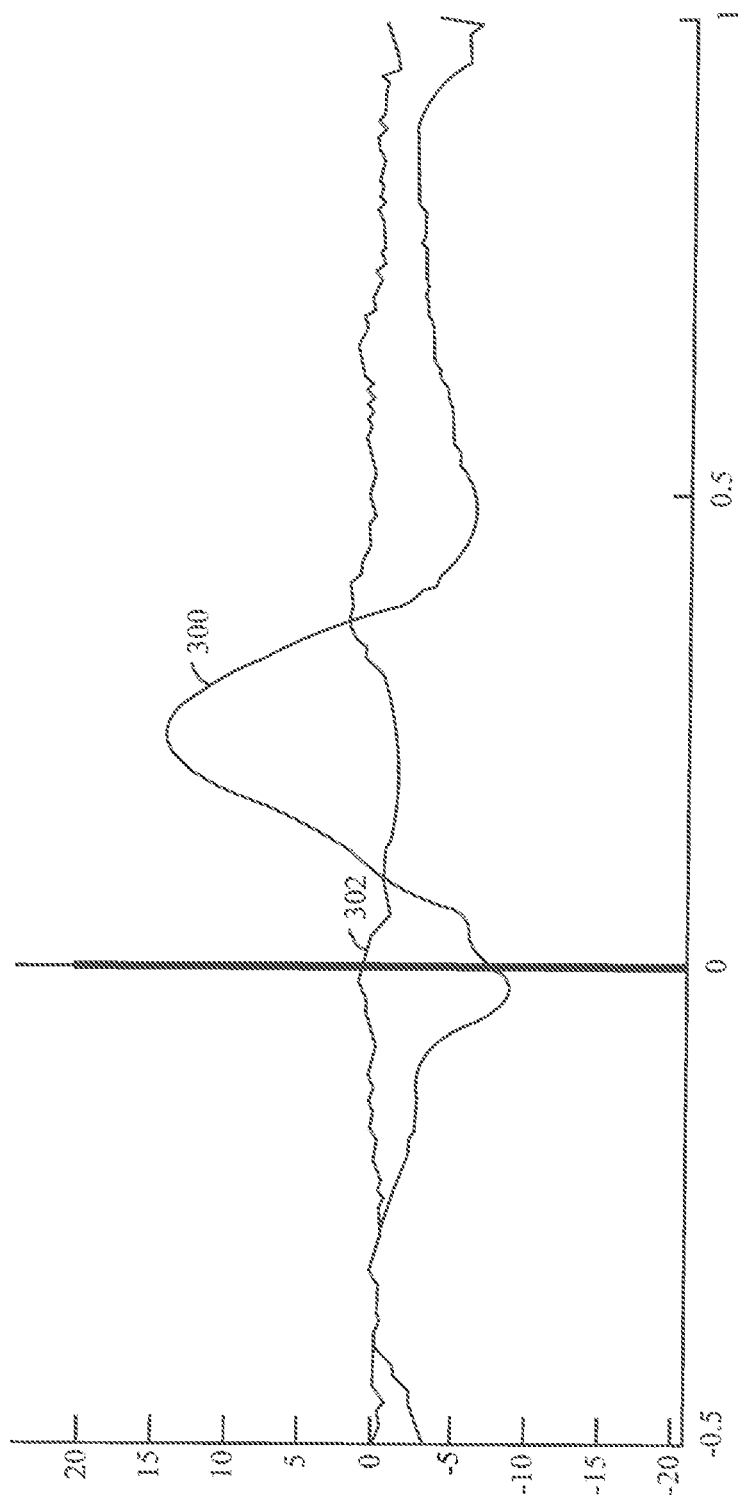
FIG. 3 illustrates a graph of implantable medical device waveform of impedance in ohms over time in seconds in accordance with embodiments herein.

Specifically, FIG. 3 illustrates example IWs 300, 302 that in example embodiments are collected using the ICM of FIGS. 1-2. In one example embodiment the IWs 300, 302 are formed by processing impedance data to separate the IWs 300, 302. In an example embodiment the IW 300 is generated from a measurement taken from a canine and IW 302 is generated from measurements taken from the same canine undergoing pacing induced heart failure. In an example the impedance data is received from an alternating current (AC) signal. The graph of FIG. 3 specifically compares impedance in ohms over time. Therefore, the first impedance waveform 300 represents a first impedance waveform during normal sinus rhythm whereas the second impedance waveform 302 represents an IW during pacing induced heart failure. As seen in this example, IWs can be affected by the left ventricular (LV) function of the heart. Still, in the majority of ICM patients, LV function is expected to be relatively stable, thus the changes in IWs are due to the changes in pocket environment.

Figure 4A:
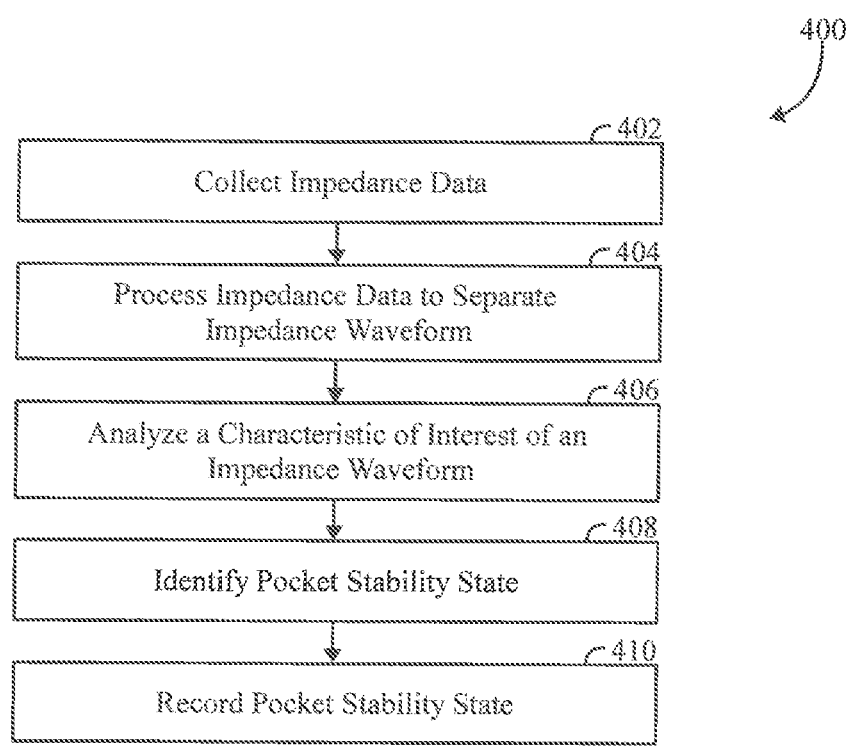
FIG. 4A illustrates a block diagram of operation of an implantable medical device or external instrument operated in accordance with embodiments herein.
Figure 6:
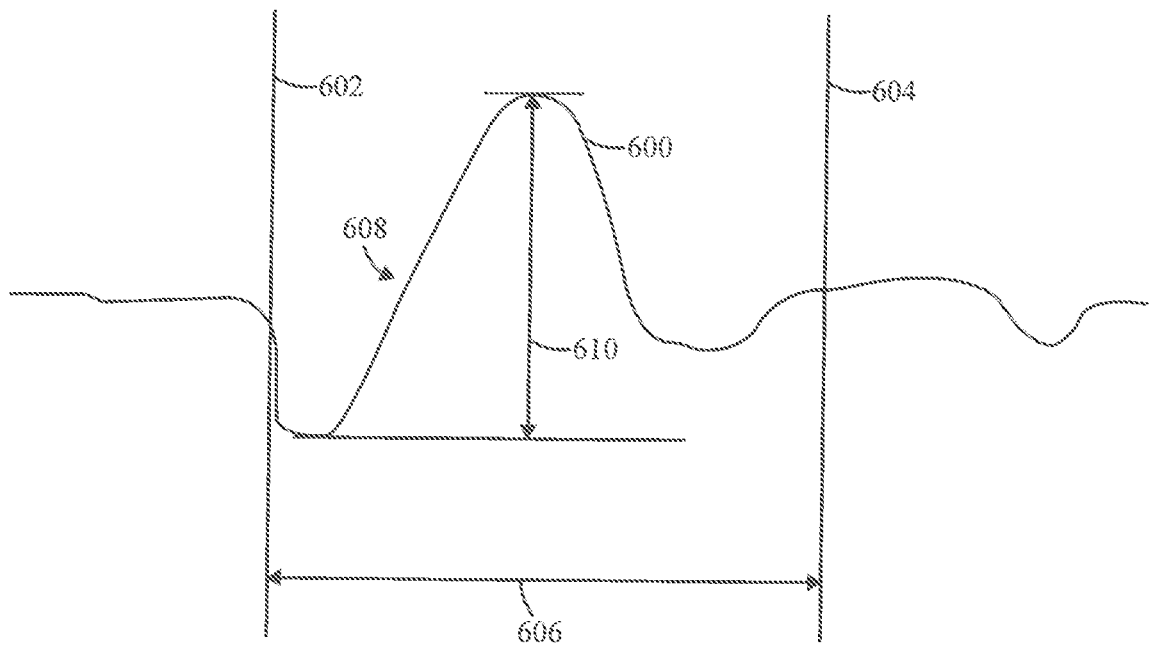
FIG. 6 illustrates a graph of implantable medical device waveform of impedance in ohms over time in accordance with embodiments herein.

FIG. 4A illustrates a method 400 of monitoring a pocket that receives ICM impedance data to form a base-line IW. In one example embodiment, the ICM is ICM 100 of FIGS. 1-2. In another example embodiment an external device such as an external device programmer, or external instrument (EI), communicates with an ICM to receive the impedance data, where in one example the EI or external device is the external device or EI 154 of FIGS. 1-2. Additionally, the IWs formed in example embodiments are the IWs 300 and 302 of FIG. 3, or the IW 600 of FIG. 6.

At 402, a processor of the ICM or an external device communicating with the ICM collects impedance data over at least one cardiac cycle. In one example the impedance data is based on a received alternating current signal. In this manner the processor establishes a base-line or first IW using the methodology as described in relation to FIG. 4A. In one example, the base-line IW is established by the processor at the time of a wound check visit. In this manner the pocket healing process is complete, giving a suitable base-line IW. While in one example the base-line IW is established in a single visit, alternatively, the base-line IW is established during pre-determined intervals or time periods, during routine check-ups, or the like. Such pre-determined intervals or time periods can be over multiple days, week, months, and the like. Specifically, the base-line IW may be formed from numerous iterations, or from collections of data from a patient processed over numerous check-ups, visits, events, and the like. Additionally and alternatively, the base-line IW may be collected from historical data within a memory of the IMD, external device, or within the cloud. Such historical data may include IW characteristics such as morphology data, including morphology data associated with the patient during previous check-ups, visits, events, and the like, or alternatively morphology data associated with other patients similarly situated to the current patient. As examples, morphology data associated with other patients of the same gender, weight, age, and the like may be included in the historical data and utilized as a base-line IW or utilized in forming a base-line IW.

As an additional example, the impedance monitoring, or collection of impedance data can also be performed when pre-determined events or conditions are met, such as when patients are lying in supine position without any activity. Such conditions can be determined by an accelerometer available in the ICM devices, or similar ICM sensors or monitoring devices. In each example, the impedance data is collected from measurements or readings taken at a time no pause or stoppage of the heart is detected, and the patient exhibits desired posture and desired heart-rate to maximize the quality of the impedance data utilized to form the base-line IW. Therefore, in each example, a processed IW is established with each reading, or iteration, and the processed IW is then utilized in forming the base-line IW.

At 404, the processor of the ICM or an external device communicating with the ICM processes the impedance data to separate an IW that varies over the at least one cardiac cycle in a manner representative of cardiac functionality over the at least one cardiac cycle. In one example, the IW separated is a base-line IW resulting from a first reading or examination after insertion of the ICM. In yet another example, the separate IW is utilized in association with historical data to form the base-line IW. Additionally and alternatively, the IW separated is one of a plurality of IWs utilized in forming the base-line IW.

At 406, the processor of the ICM or an external device communicating with the ICM analyzes a characteristic of interest from the IW separated from the impedance data at 404 over the cardiac cycle. The characteristic of interest includes waveform slope, amplitude, peak-to-peak ratio, or the like. Specifically, any characteristic of the waveform that independently or in combination with other waveform characteristics that can be used to characterize the pocket stability of the ICM is included.

Figure 4B:
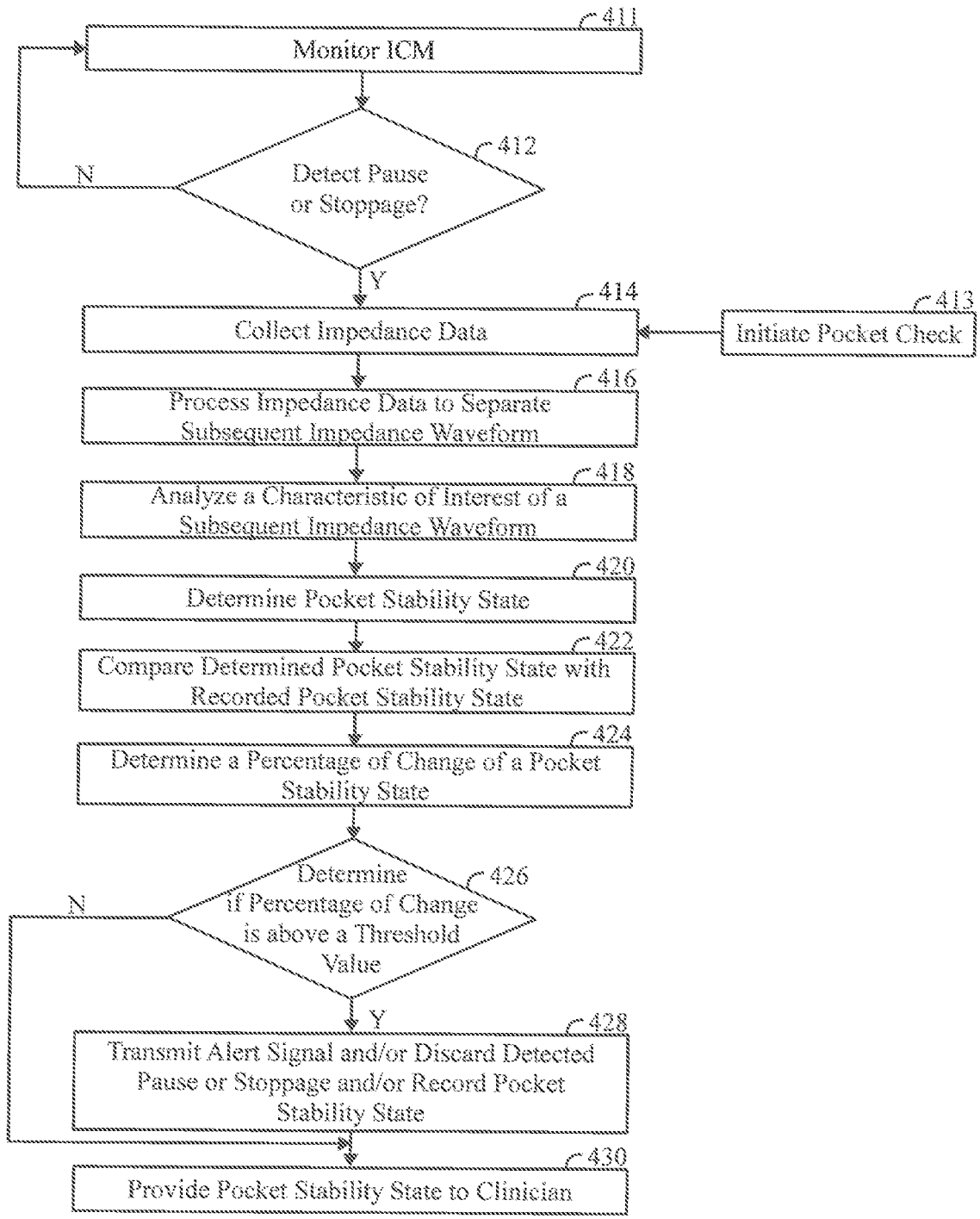
FIG. 4B illustrates a block diagram of operation of an implantable medical device or external instrument operated in accordance with embodiments herein.

At 408, the processor of the ICM or an external device communicating with the ICM determines the pocket stability state of the ICM, based on the separated IW, including the analysis of the characteristic of interest to form the base-line IW. At 410, the processor of the ICM or an external device communicating with the ICM records the pocket stability state of the ICM and base-line IW at that time. FIG. 4B illustrates how after determining and forming the base-line IW and pocket stability, the monitoring system may be utilized to determine changes in pocket stability and used to minimize and prevent mis-diagnosis as a result of changes in pocket stability. At 411, the processor of the ICM or an external device communicating with the ICM monitors the ICM for a pre-determined condition including heart arrythmias such as AFs, and Brady episodes.

At 412, the processor of the ICM or an external device communicating with the ICM determines if a pause, or stoppage that is indicative of an arrhythmia or Brady episode. In one example, the processor receives and records electrocardiogram (EGM) signals at electrodes provided on a housing of the ICM. Based on the recorded EGM signals, the processor detects a pause or stoppage. If the processor does not detect a pause or stoppage, then the processor of the ICM or an external device communicating with the ICM continues to monitor the ICM for a pre-determined condition including heart arrythmias and Brady episodes.

Optionally, at 413, a pocket check is initiated at a time after the base-line IW and pocket stability are determined such that the ICM collects impedance data over at least one cardiac cycle. The pocket check may be at a routine checkup set up at a pre-determined interval of time, periodically when a patient is lying in supine position without any activity, and the like. Such periodic intervals, pre-determined intervals of time, and predetermined events may be over days, weeks, months, or the like. Regardless, the processor determines a subsequent IW to the base-line IW.

At 414, if at 412 a pause or stoppage is detected, the processor of the ICM or an external device communicating with the ICM collects impedance data over at least one cardiac cycle. In one example the impedance data is based on a received alternating current signal. Specifically, the impedance data tracks, or is indicative of cardiac function and therefore waveform variables such as QRS features are identifiable in the impedance waveform, even when EGM signals or data is not available. In this manner, data from an EGM guided cardiac cycle is unneeded, and instead variables such as amplitude of the impedance waveform may be instead utilized. In this manner the processor determines a subsequent IW to the base-line IW. In both 413 and 414, the subsequent IW is established at a time period after the base-line IW in order to make a determination regarding change in pocket stability based on the subsequent IW. In one example the overall summation of the waveform signal over a certain period is determined and compared to a summation difference. In this way an EGM guided cardiac cycle is not relied on and instead signal amplitude measurements are utilized. Specifically, at 414, because the pause or stoppage, such as detected in relation to an arrythmia or Brady episode, is only a temporary pause or stoppage, the cardiac cycle continues. Thus, 412, and 413 are provided to indicate different reasons for determining the subsequent IW. While processing impedance data to form a subsequent IW in relation to a detected pause or stoppage from EGMs, or processing impedance data to form a subsequent IW at a regularly scheduled appointment are two reasons for determining or forming the subsequent IW, other reasons are also contemplated. As an additional example, if a patient is feeling chest pains and visits a clinician, even if a pause or stoppage is not detected, impedance data may be processed, and a subsequent IW may be formed at that time to determine if a pocket change has occurred and/or to provide a new base-line IW if desired. By utilizing impedance waveforms, the clinician is provided with additional information in diagnosing the reason for the chest pain. Specifically, the determination may result in avoiding unneeded and expensive medical procedures, saving time and cost.

At 416, the processor of the ICM or an external device communicating with the ICM processes the impedance data to separate the subsequent IW that varies over the at least one cardiac cycle in a manner representative of cardiac functionality over the at least one cardiac cycle. At 418, the processor of the ICM or an external device communicating with the ICM analyzes a characteristic of interest from the second impedance waveform over the cardiac cycle. The characteristic of interest includes both morphology characteristics and timing characteristics and includes waveform shape, waveform slope, amplitude, peak-to-peak ratio, and the like. Specifically, any characteristic of the subsequent IW that independently or in combination with other characteristics that can be used to characterize the pocket stability of the ICM is included. In one example, the processor analyzes the same characteristic of interest at 418 as is analyzed in relation to the base-line IW at 406.

At 420, the processor determines the pocket stability state of the ICM based on a comparison of the subsequent IW and the base-line IW. In the example embodiment wherein a pause, or stoppage is detected at 412, the determination is made to ensure the pause, or stoppage is not a result of pocket instability or changes. In the example embodiment wherein the subsequent IW is determined at a pre-determined interval or during a predetermined event, the determination can provide an indication of a probability of a false reading so that preventive measures may be undertaken.

At 422, the processor of the ICM or an external device communicating with the ICM compares the determined pocket stability state at 420 with the recorded pocket stability state provided at 410. In one example embodiment, the processor of the ICM or external device communicating with the ICM compares the base-line IW to the subsequent IW. In an example, the morphology of the base-line IW is matched against the morphology of the subsequent IW. Alternatively and additionally, in one example, the characteristic of interest of the base-line IW is compared to the characteristic of interest of the subsequent IW. The characteristics of interest as previously described include both morphological characteristics and timing characteristics, including, waveform shape, waveform slope, amplitude, peak-to-peak ratio, or the like.

At 424, based on the comparison, the processor of the ICM or an external device communicating with the ICM determines a percentage of change in the pocket stability state between the determined pocket stability state at 414 and the recorded pocket stability state provided at 410. In one example, this determination is made based on changes related to both morphological characteristics and timing characteristics, including, waveform shape, waveform characteristic such as change in slope angle, change in amplitude, change in peak-to-peak value, or the like. Included also is the matching of morphology of the base-line IW compared to the subsequent IW. Alternatively, more than one waveform characteristic is considered, and an algorithm determines the percent change in the pocket stability state based on multiple waveform characteristics.

At 426, a processor of the ICM or an external device communicating with the ICM determines if changes in the pocket stability state are above a threshold value. In one example, the threshold value is at fifty percent (50%) or greater change in the pocket stability state. This includes a 50% or greater change in the base-line IW compared to the subsequent IW, or a 50% or greater change in a characteristic of interest of the base-line IW compared to a characteristic of interest of the subsequent IW.

By exceeding the threshold value, there is an increased probability that the signal being transmitted is experiencing degradation. Thus, an increased probability of a false arrhythmia or false Brady episode is likely in the example embodiment where a pause or stoppage is detected at 412; whereas in the example embodiment where the subsequent IW is determined at a pre-determined interval, or during a pre-determined event, the probability is increased a false pause or stoppage may be detected in the future by the ICM such that preventative measure may be undertaken.

At 428, responsive to the change in the pocket stability state exceeding the threshold value, a processor of the ICM or an external device communicating with the ICM takes preventive action. In one example embodiment when a pause or stoppage is detected at 412, the processor of the ICM or an external device communicating with the ICM outputs an indicator to a user or clinician that the threshold value has been exceeded. In one example an alert is provided by transmitting a signal to be electronically communicated to a user or clinician that the pause or stoppage is likely the result of pocket instability and not an arrhythmia, Brady episode, or the like. For purposes of this disclosure, the term "electronic communication" may be defined to include both wired and wireless connections. In this manner an alert signal is communicated to a clinician indicating the degradation in the transmitted signal and the potential for a false reading. The communication can include a message displayed on a display, a light indicator, voice command, or the like. In this manner, a clinician is able to more accurately diagnose the cause of the pause or stoppage.

In one example, when electrocardiogram (EGM) signals are recorded at electrodes provided on the housing of and ICM as described in relation to 412, responsive to the change in the pocket stability state exceeding the threshold value, an indicator is outputted that an ICM has shifted within an implant pocket and is experiencing degradation of signal quality of the EGM signals. Therefore, responsive to the false indication of the pause or stoppage, the indicator is outputted for the clinician, preventing unneeded tests and procedures, and saving cost, time, and anxiety. Additionally and alternatively, in an example embodiment at 428, when a pause or stoppage is detected at 412, the processor of the ICM or an external device communicating with the ICM transmits a signal to discard or ignore the detected pause or stoppage. The signal to discard or ignore the detected pause or stoppage may be sent prior to a signal being transmitted that a pause or stoppage has occurred, thus preventing the signal that a pause or stoppage has been detected from being transmitted, or may be transmitted after the signal is transmitted that a pause or stoppage has been detected so a clinician may make a final determination that the signal indicating the pause or stoppage should be ignored. In either case, in an example, when a determination is made a detected pause or stoppage should be discarded or ignored, a label, indicia, or record of the determination is created and recorded. Specifically, the pocket stability and IW comparison information may be stored and displayed with other medical information associated with the pause or stoppage for consideration by the clinician.

In one example, at 430 the pocket stability information is provided or displayed to the clinician even if a threshold value is not exceeded. Consequently, when the pocket stability is near the threshold value, but does not exceed the threshold value, the clinician may be informed of the potential of the false pause or stoppage indication and make determinations accordingly.

Additionally and alternatively, in an example embodiment when the threshold value is exceeded during a measurement taken at a pre-determined interval or a pre-determined event, thus indicating a potential false pause or stoppage could be detected, the alert signal may be transmitted to the clinician indicating the change in pocket stability, and that EGM signals could experience degradation as a result of the change in pocket stability. Additionally and alternatively, even when the threshold value is not exceed at 430, the change in pocket stability is displayed for use by a clinician. By evaluating the IWs and consequently the pocket stability state at predetermined intervals of time or during predetermined events, pocket changes may be determined prior to the pocket change resulting in the detection of a pause or stoppage caused by the pocket change. Consequently, preventative measures may be undertaken to correct the movement of the ICM in the pocket, or other detected pocket changes prior to the pocket change resulting in a detection of a pause or stoppage.

Figure 5:
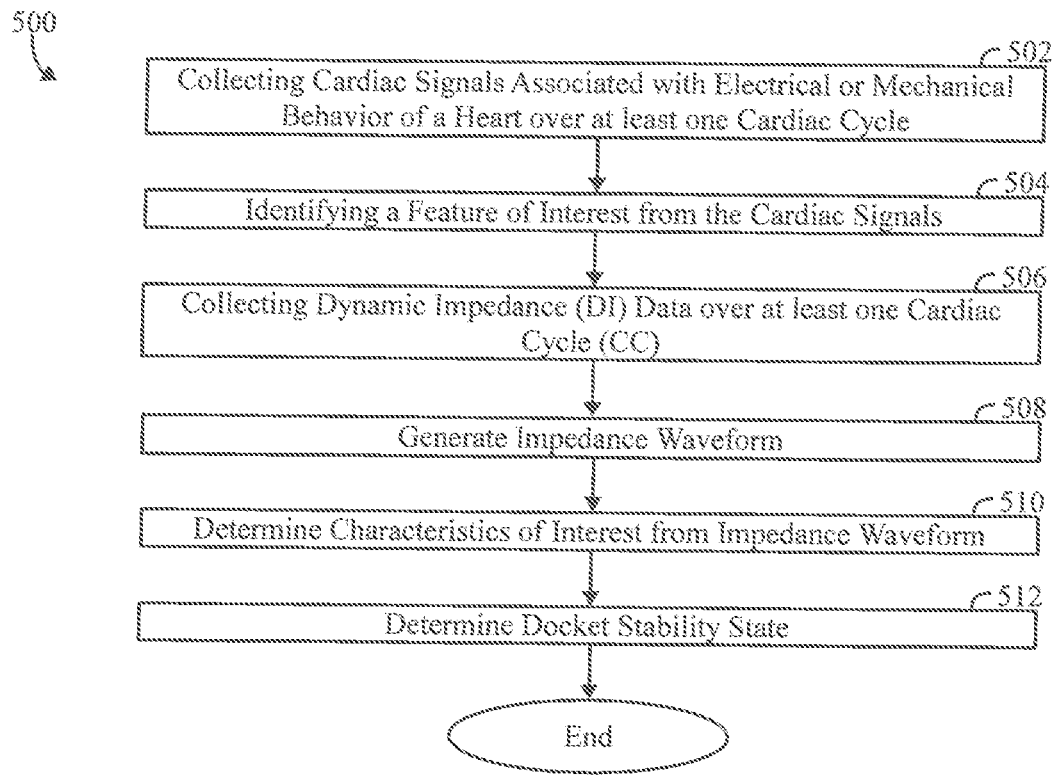
FIG. 5 illustrates a block diagram of a cardiac function characterization method in accordance with embodiments herein

FIG. 5 illustrates a method 500 for collecting and analyzing impedance data to determine a pocket stability state to be carried out in accordance with an embodiment by one or more of an ICM, including the ICM of FIGS. 1-2, or external programmer such as the external device or EI 154 of FIGS. 1-2, described herein. Similarly, this method 500 in one example is utilized to collect and analyze impedance data in association with the method 400 of FIG. 4.

At 502, a processor of the ICM collects cardiac signals associated with electrical and/or mechanical behavior of a heart over at least one cardiac cycle. For example, the cardiac signals may be IEGM signals, electrocardiogram (EKG) signals, and the like. The cardiac signals may be collected from external skin electrodes, implanted electrodes or the like.

At 504, the processor identifies features of interest (FOI) from the cardiac signals. The FOIs include both timing features and morphological features. For example, one FOI may be the peak of the R-wave, the start or center of the P-wave, the ST segment, and the like, where an R-wave is the first positive deflection of a wave, the P-wave is the first deflection of the wave, and ST segment is the electrically neutral period of in an electrocardiogram (ECG) between the QRS complex and a T-wave. The timing feature may be intrinsic (e.g., a naturally occurring cardiac event) or paced (e.g., a paced R-wave, a paced P-wave, etc.). When the cardiac signal is indicative of mechanical behavior, the timing feature of interest may represent the amount of movement (indicative of exercise), the orientation of the patient with respect to gravity (prone, supine, standing, etc.) and the like.

At 506, the processor collects the impedance data for a collection window over at least one cardiac cycle. Optionally, different electrode combinations may be used to collect subsets of the impedance data, where each subset of impedance data may be analyzed as described herein.

At 508, an impedance waveform is obtained utilizing the impedance data. The waveform in one example is separated form an AC waveform. In an example embodiment, the IW may include mechanical components that occur during an R-wave, P-wave, and a T-wave. At 510, characteristics of interests are determined from the generated IW. This includes maximum slope of the IW, peak-to-peak value of the IW, and the like.

At 512, the pocket stability state is determined utilizing the IW and characteristics of interest determined. In one example embodiment, the IW morphology is utilized to determine the pocket stability state. In another example embodiment, a single characteristic of interest is utilized to determine the pocket stability state. In yet another example embodiment, at least two characteristics of interest are utilized to determine the pocket stability state. Thus, based on the impedance data, the pocket stability state can be determined at any given time such that when comparing the pocket stability state at a first time, such as during a wound check, and the pocket stability state at a second time, such as a follow up appointment, a change in pocket stability state may be determined. As a result, procedures may be undertaken to prevent the movement from resulting in a false detection of an arrhythmia or brady episode or arrhythmia episode detection is made with the pocket stability information.

FIG. 6 illustrates a graph again showing an IW 600 as a function of ohms versus time and example characteristics of interest that may be utilized to determine the pocket stability state. In one example embodiment the IW 600 is formed by processing impedance data to separate the IW 600. In an example the impedance data is received from an alternating current based signal. Specifically, cardiac components of the IW 600 are extracted to track the changes in pocket characteristics. Here, cardiac mechanical markers 602, 604, such as R-wave markers are available from ICMs, and features, and are extracted during a predetermined duration 606 after each R-wave. For example, in FIG. 6, various features during one cardiac cycle are extracted during 500 msecs indicated by markers 602 and 604. In other examples the duration 606 is in a range between 300 msecs and 600 msecs depending on heart rate. Thus, characteristics and features of the IW 600 can be determined such as the maximum slope 608 of the IW 600, or peak-to-peak value 610 of the IW 600. Additional features include determining the mean absolute derivative of an IW 600 to capture the jaggedness, or noisiness of a give IEGM can be provided. Additionally, a mean absolute value can also be determined to capture the size of the waveform.

Thus, provided is a computer implemented method for detecting pocket stability for an IMD such as an ICM. One or more processors collect impedance data over cardiac cycles and process the impedance data to separate a first impedance waveform that varies over a cardiac cycle in a manner representative of cardiac functionality over the cardiac cycle. A characteristic of interest from the first impedance waveform over the cardiac cycle is then analyzed to identify and record pocket stability state of an IMD, such as an ICM. Based on the pocket stability state, or based on a subsequent or second pocket stability state of the ICM compared to the recorded or first pocket stability state, identification of a change in the pocket stability state is provided. Consequently, a clinician or user is able to recognize and address change in the pocket stability state during diagnosis and treatment.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method for detecting pocket stability for an implantable cardiac monitor (ICM) within a subcutaneous pocket, the method comprising:
   under control of one or more processors in the ICM,
   collecting impedance data over at least one cardiac cycle
   processing the impedance data to separate an impedance waveform that varies over the at least one cardiac cycle in a manner representative of cardiac functionality over the at least one cardiac cycle;
   analyzing a characteristic of interest from the impedance waveform over the at least one cardiac cycle to determine movement of the ICM within the subcutaneous pocket; and
   identifying and recording a pocket stability state of the ICM based on the analyzing operation and the movement.

2. The method of claim 1, further comprising, recording electrocardiogram (EGM) signals at electrodes provided on a housing of the ICM and detecting a pause or stoppage based on the recorded EGM signals.

3. The method of claim 2, wherein processing the impedance data to separate a subsequent impedance waveform, and comparing the subsequent impedance waveform to the base-line impedance waveform that is based on the processed impedance waveform, is responsive to the ICM detecting the pause or stoppage.

4. The method of claim 3, further comprising:
   determining whether the pause or stoppage is false by comparing the subsequent impedance waveform to the base-line impedance waveform;
   outputting an indicator that the ICM has shifted within an implant pocket and is experiencing degradation of signal quality of the EGM signals when the pause or stoppage is false; and
   discarding the detected pause or stoppage when the pause or stoppage is false.

5. The method of claim 4, further comprising, wherein the indicator is an alert signal that provides a communication from the ICM related to the change in pocket stability state.

6. The method of claim 5, wherein the communication is displayed on a display of the ICM with a label formed based on comparing the base-line impedance waveform and subsequent impedance waveform.

7. The method of claim 1, further comprising processing the impedance data to separate a subsequent impedance waveform; and comparing the subsequent impedance waveform to a base-line impedance waveform that is based on the processed impedance waveform.

8. The method of claim 7, wherein comparing the subsequent impedance waveform to the base-line impedance waveform comprises comparing the characteristic of interest from the processed impedance waveform and a characteristic of interest from the subsequent impedance waveform to determine a change in the pocket stability state of the ICM.

9. The method of claim 8, wherein the characteristic of interest of the processed impedance waveform is at least one of a morphology characteristic or a timing characteristic.

10. The method of claim 1, wherein the impedance waveform is based on an alternating current (AC) based signal.

11. The method of claim 1, wherein the impedance data is collected between a combination of electrodes configured to be located in the subcutaneous pocket with the ICM.

12. The method of claim 1, wherein the pocket stability state indicates when the ICM has changed location within the subcutaneous pocket relative to an initial implant position through at least one of i) moving up or down; ii) moving left or right (strafing/swaying); iii) moving forward and backward (walking/surging); iv) swiveling left and right (yawing); v) tilting forward and backward (pitching); vi) rotation clockwise and counterclockwise; and vii) pivoting side to side (rolling).

13. A monitoring system for detecting pocket stability for an implantable cardiac monitor (ICM) within a subcutaneous pocket, comprising:
   an ICM including a housing and one or more processors for receiving impedance data generated by an alternating current (AC) signal of the ICM and configured to:
     separate from the data generated by the AC signal an impedance waveform that varies over the at least one cardiac cycle in a manner representative of cardiac functionality over the at least one cardiac cycle;

analyze a characteristic of interest from the impedance waveform over the at least one cardiac cycle to form a base-line impedance waveform;

analyze the characteristic of interest from the impedance waveform over at least one additional cardiac cycle, relative to the base-line impedance waveform, to determine movement of the ICM within the subcutaneous pocket and identify and record a pocket stability state of the ICM based on the characteristic of interest and the movement.

14. The monitoring system of claim 13, wherein the one or more processors are further configured to:

record electrocardiogram (EGM) signals at electrodes provided on the housing of the ICM;

detect a pause or stoppage based on the recorded EGM signals;

determine whether the pause or stoppage is false by comparing the subsequent impedance waveform to the base-line impedance waveform;

output an indicator that the ICM has shifted within an implant pocket and is experiencing degradation of signal quality of the EGM signals when the pause or stoppage is false.

15. The monitoring system of claim 14, wherein the one or more processors is further configured to, prior to outputting the indicator, process the impedance data to separate a subsequent impedance waveform; and compare the subsequent impedance waveform to the base-line impedance waveform.

16. The monitoring system claim 15, wherein the one or more processors is further configured to, determine a change in pocket stability state based on the comparison of the subsequent impedance waveform to the base-line impedance waveform; and responsive to the change in pocket stability state of the ICM, transmit an alert signal to provide a communication from the ICM related to the change in pocket stability state.

17. The monitoring system of claim 16, wherein the change in pocket stability state of the ICM is above a threshold value.

18. The monitoring system of claim 13, further comprising a combination of electrodes configured to be located in the subcutaneous pocket with the ICM, the data collected between the combination of electrodes.

19. The monitoring system of claim 13, wherein the pocket stability state indicates when the ICM has changed location within the subcutaneous pocket relative to an initial implant position through at least one of i) moving up or down; ii) moving left or right (strafing/swaying); iii) moving forward and backward (walking/surging); iv) swiveling left and right (yawing); v) tilting forward and backward (pitching); vi) rotation clockwise and counterclockwise; and vii) pivoting side to side (rolling).

* * * * *